(12) United States Patent
Sagata

(10) Patent No.: US 9,911,447 B2
(45) Date of Patent: *Mar. 6, 2018

(54) FLUOROPOLYETHER COMPOUND, AND LUBRICANT AND MAGNETIC DISC COMPRISING SAME

(71) Applicant: MORESCO Corporation, Hyogo (JP)

(72) Inventor: Ryosuke Sagata, Hyogo (JP)

(73) Assignee: MORESCO CORPORATION, Hyogo (JP)

(*) Notice: Subject to any disclaimer, the term of this patent is extended or adjusted under 35 U.S.C. 154(b) by 280 days.

This patent is subject to a terminal disclaimer.

(21) Appl. No.: 14/764,600

(22) PCT Filed: Oct. 9, 2014

(86) PCT No.: PCT/JP2014/077624
§ 371 (c)(1),
(2) Date: Jul. 30, 2015

(87) PCT Pub. No.: WO2015/087615
PCT Pub. Date: Jun. 18, 2015

(65) Prior Publication Data
US 2015/0371672 A1 Dec. 24, 2015

(30) Foreign Application Priority Data
Dec. 9, 2013 (JP) ................. 2013-254202

(51) Int. Cl.
G11B 5/66 (2006.01)
G11B 5/725 (2006.01)
C07C 43/23 (2006.01)
C10M 105/54 (2006.01)
(Continued)

(52) U.S. Cl.
CPC ............ G11B 5/725 (2013.01); C07C 43/23 (2013.01); C08G 65/34 (2013.01);
(Continued)

(58) Field of Classification Search
CPC .. G11B 5/725; C08G 2650/48; C08G 65/007; C09D 171/02; C10M 107/38;
(Continued)

(56) References Cited

U.S. PATENT DOCUMENTS 8,734,966 B2 * 5/2014 Sagata ................. G11B 5/725
428/835.8
2002/0183211 A1 12/2002 Akada et al.
(Continued)

FOREIGN PATENT DOCUMENTS

JP 2010-143855 7/2010

OTHER PUBLICATIONS

International Search Report dated Jan. 6, 2015 in International (PCT) Application No. PCT/JP2014/077624.
Kasai et al., "Disk Lubricants for Spontaneous Adsorption and Grafting to Carbon Overcoat by UV Irradiation", Tribol Lett., vol. 38, Apr. 3, 2010, pp. 241-251.
Kasai et al., "Bonding of Hard Disk Lubricants with OH-Bearing End Groups", Tribol Lett., vol. 46, Jan. 26, 2012, pp. 43-47.

*Primary Examiner* — Holly C Rickman
(74) *Attorney, Agent, or Firm* — Wenderoth, Lind & Ponack, L.L.P.

(57) ABSTRACT

A compound of the formula (1), lubricant containing the compound and magnetic disk $$R^1-C_6H_4O-CH_2CH(OH)CH_2OCH_2-R^2-CH_2-O-CH_2CH(OH)CH_2-OC_6H_4-R^1 \quad (1)$$

wherein $R^1$ is alkoxyl having 1 to 4 carbon atoms, amino or amido, $R^2$ is $-CF_2CF_2O(CF_2CF_2CF_2O)_zCF_2CF_2-$ or $-CF_2CF_2CF_2O(CF_2CF_2CF_2CF_2O)_nCF_2CF_2CF_2-$, z is a real number of 1 to 15, n is a real number of 0 to 4.

8 Claims, 1 Drawing Sheet

(51) Int. Cl.
*C10M 107/38* (2006.01)
*C08G 65/34* (2006.01)

(52) U.S. Cl.
CPC ........ *C10M 105/54* (2013.01); *C10M 107/38* (2013.01); *C10M 2211/0425* (2013.01); *C10M 2213/0606* (2013.01); *C10N 2230/10* (2013.01); *C10N 2230/74* (2013.01); *C10N 2240/204* (2013.01); *C10N 2250/121* (2013.01)

(58) Field of Classification Search
CPC ...... C10M 2213/06; C10M 2213/0606; C10N 2040/18; C10N 2240/204
See application file for complete search history.

(56) References Cited

U.S. PATENT DOCUMENTS

| | | |
|---|---|---|
| 2008/0020171 A1 | 1/2008 | Wakabayashi et al. |
| 2010/0261039 A1 | 10/2010 | Itoh et al. |
| 2012/0002323 A1 | 1/2012 | Kato et al. |
| 2012/0315504 A1 | 12/2012 | Shimizu et al. |
| 2013/0209837 A1 | 8/2013 | Sagata et al. |
| 2013/0288080 A1* | 10/2013 | Yan ..................... C07F 9/65815 428/833 |
| 2017/0152456 A1* | 6/2017 | Sagata ................ C10M 105/54 |

* cited by examiner

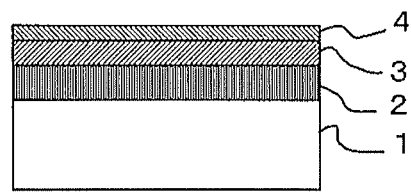

FLUOROPOLYETHER COMPOUND, AND LUBRICANT AND MAGNETIC DISC COMPRISING SAME

TECHNICAL FIELD

The present invention relates to fluoropolyether compounds having an aromatic group, lubricants containing the compound and magnetic disks having the lubricant applied thereto.

BACKGROUND ART

With an increase in the recording density of magnetic disks, the distance between the magnetic disk serving as a recording medium and the magnetic head for use in recording of information or playback has become almost nil close to contact therebetween. The magnetic disk is provided over the surface thereof with a carbon protective film or lubricant film for the purpose of diminishing abrasion due to the contact or sliding of the magnetic head thereon or preventing contamination of the disk surface.

The carbon protective film is produced generally by the sputtering process or CVD process. The disk surface is protected with the two films, i.e., the carbon protective film and the lubricant film thereover.

The lubricants generally in use are fluoropolyethers having functional groups. Examples of functional groups are hydroxyl, cyclophosphazene and amino groups (Patent Literature 1, 2). Particularly, lubricants having a phosphazene group are materials having high resistance to decomposition and known as materials for giving high durability to magnetic disks (for example, Patent Literature 1, 2).

In a heat-assisted (thermally assisted) hard disk drive which is presently developed, a technology is employed in which the disk is locally heated by a laser. When a lubricant is used in such circumstance, the functional group moiety such as hydroxyl group, cyclophosphazene group or amino group easily causes decomposition by the heat of the laser. In addition, the fluoropolyether also decomposes by heat. Due to these decomposition, the lubricant on the disk is transferred to a magnetic head (pick up), and it becomes the problem to cause malfunction.

On the other hand, a lubricant containing a compound which has a perfluoropolyether main chain and an aromatic group in the molecular terminal is known as a lubricant which is excellent in durability of magnetic disk, particularly in LUL durability and resistance to alumina (Patent Literature 3). However, only fluoropolyether having —(CF$_2$O)n(CF$_2$CF$_2$O)m-structure (Fomblin structure) in the molecular main chain is concretely disclosed as a compound of Patent Literature 3. This compound is demanded to have still more superior heat resistance as mentioned later (Patent Literature 3).

Patent Literature 1: JP Patent No. 4137447
Patent Literature 2: JP Patent No. 4570622
Patent Literature 3: JP 2009-266360A An object of the present invention is to provide a lubricant having superior heat resistance which does not cause decomposition under high temperature and is not transferred to a magnetic head, and magnetic disks.

SUMMARY OF THE INVENTION

The present invention provides the following.
1. A compound of the formula (1)

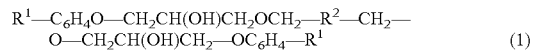

$$R^1-C_6H_4O-CH_2CH(OH)CH_2OCH_2-R^2-CH_2-O-CH_2CH(OH)CH_2-OC_6H_4-R^1 \quad (1)$$

wherein $R^1$ is alkoxyl having 1 to 4 carbon atoms, amino or amido, $R^2$ is —CF$_2$CF$_2$O(CF$_2$CF$_2$CF$_2$O)$_z$CF$_2$CF$_2$— or —CF$_2$CF$_2$CF$_2$O(CF$_2$CF$_2$CF$_2$O)$_n$CF$_2$CF$_2$CF$_2$—, z is a real number of 1 to 15, n is a real number of 0 to 4.
2. A lubricant containing a compound of the formula (1).
3. A magnetic disk comprising at least a recording layer and a protective layer formed over a substrate, and a lubricating layer formed over the resulting surface, the lubricating layer containing a compound of the formula (1).

EFFECT OF THE INVENTION

The fluoropolyether compounds of the invention having an aromatic group are highly stable to heat compared with the conventionally used compounds having —(CF$_2$O)n (CF$_2$CF$_2$O)m-structure (Fomblin structure). Thus, it is possible to provide a lubricating film which is hardly deteriorated with use under high heat environment for a long period of time.

EMBODIMENT OF PRACTICING THE INVENTION

Process for Preparing the Lubricant

The lubricant of the formula (1) according to the invention is obtained by reacting, for example, a fluoropolyether (a) having hydroxyl at opposite terminals with a phenoxy compound having an epoxy group. Stated more specifically, the compound is prepared by the following process.

The fluoropolyether (a) having hydroxyl at opposite terminals can be, for example, a compound of the formula HOCH$_2$CF$_2$CF$_2$O(CF$_2$CF$_2$CF$_2$O)$_z$CF$_2$CF$_2$CH$_2$OH or HOCH$_2$CF$_2$CF$_2$CF$_2$O(CF$_2$CF$_2$CF$_2$CF$_2$O)$_n$CF$_2$CF$_2$CF$_2$CH$_2$OH.

The fluoropolyether is 500 to 2000, preferably 800 to 1500, in number average molecular weight. The number average molecular weight mentioned is a value measured by $^{19}$F-NMR using JNM-ECX400, product of JEOL Ltd. For NMR measurement, the sample itself was used without dilution with a solvent. As a reference for chemical shift, a known peak was used which is a portion of fluoropolyether skeleton structure. z is a real number of 0 to 15, preferably 1 to 10, and when z is a real number of 1 to 10, molecular chain is more flat and preferable. n is a real number of 0 to 4.

The fluoropolyether (a) is a compound having a molecular weight distribution. The molecular weight distribution (PD), which is weight average molecular weight/number average molecular weight, is 1.0 to 1.5, preferably 1.0 to 1.3, and more preferably 1.0 to 1.1. The molecular weight distribution is a characteristic value obtained by using HPLC-8220GPC, product of Tosoh Co., Ltd., column (PLgel Mixed E), product of Polymer Laboratories, eluent which is HCFC-type alternative CFC and a non-functional perfluoropolyether serving as a reference material.

(2) Synthesis of Lubricant of the Invention

The straight-chain fluoropolyether (a) having hydroxyl at opposite terminals is reacted with a phenoxy compound (A) having an epoxy group in the presence of a catalyst. The reaction temperature is 20 to 90° C., preferably 60 to 80° C.

The reaction time is 5 to 20 hours, preferably 10 to 15 hours. It is desirable to use the compound (A) in an amount of 1.0 to 2.0 equivalents and the catalyst in an amount of 0.05 to 0.1 equivalent, relative to the compound (a). The catalysts to be used are alkali compounds such as sodium tert-butoxide and potassium tert-butoxide. The reaction may be conducted in a solvent. Examples of solvents to be used are tert-butanol, toluene and xylene. The reaction mixture is thereafter washed, for example, with water and dewatered, whereby a compound (1) of the invention is obtained.

Examples of phenoxy compound (A) having an epoxy group is shown below. $R^1$ is alkoxyl having 1 to 4 carbon atoms, amino or amido group.

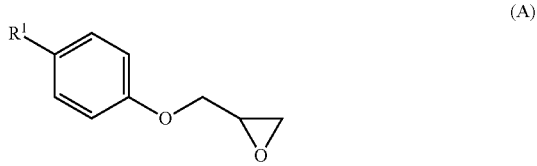

(A)

Examples of alkoxyl having 1 to 4 carbon atoms are methoxy, ethoxy, propoxy and butoxy. Examples of amino groups are amino, methylamino, dimethylamino, ethylamino and diethylamino. Examples of amido groups are acetamido and propionamido.

Examples of compound (A) are glycidyl 4-methoxyphenyl ether, glycidyl 4-ethoxyphenyl ether, glycidyl 4-propoxyphenyl ether, glycidyl 4-butoxyphenyl ether, glycidyl 4-aminophenyl ether, glycidyl 4-methylaminophenyl ether, glycidyl 4-dimethylaminophenyl ether, glycidyl 4-ethylaminophenyl ether, glycidyl 4-diethylaminophenyl ether, glycidyl 4-acetamidophenyl ether and glycidyl 4-propionamidophenyl ether.

The compound of the present invention is applied to the magnetic disk surface preferably by diluting the compound with a solvent and coating the disk surface with the diluted compound. Examples of useful solvents are PF-5060, PF-5080, HFE-7100 and HFE-7200 manufactured by 3M, Vertrel-XF, product of DuPont, etc. The concentration of the compound as diluted is up to 1 wt. %, preferably 0.001 to 0.1 wt. %.

While the compound of the invention is usable singly, the compound can be used also as mixed in a desired ratio with another material, such as Fomblin Zdol, Ztetraol, Zdol TX, AM manufactured by Solvay Solexis, Demnum manufactured by Daikin Industries, Ltd. and Krytox manufactured by DuPont.

The compound of the present invention enables the head to be spaced by a small distance from the magnetic disk inside magnetic disk devices and is useful as a lubricant for giving improved durability under a sliding condition. The compound of the invention is characterized by the interaction of the hydroxyl with the polar site present in the carbon protective film and by the interaction of the aromatic group with carbon unsaturated bonds present in the carbon protective film. Accordingly, the compound is usable as a surface protective film for magnetic heads, photomagnetic recording devices, magnetic tapes, plastics and like organic materials having a carbon protective film, and also as a surface protective film for inorganic materials such as glass and metal.

FIG. 1 shows a sectional view schematically showing the magnetic disk of the invention. The magnetic disk of the invention comprises a substrate 1, at least one recording layer 2 formed on the substrate 1, a protective layer 3 on the recording layer 2 and a lubricant layer 4 formed thereon, as an outermost layer, which contains the compound of the invention. The substrate is composed of aluminum alloy, glass and like ceramics, polycarbonate or the like.

The recording layer of the magnetic disk, i.e., the magnetic layer is composed of mainly elements capable of forming ferromagnetic bodies, such as iron, cobalt or nickel, alloy or oxide containing chromium, platinum or tantalum in addition to such elements. These materials are applied by, e.g., a plating method or a sputtering method. The protective layer is formed of carbon, SiC, $SiO_2$ or the like. The layer is formed by a sputtering method or CVD method.

Lubricant layers presently available are up to 20 Å in thickness, so that when a lubricant having a viscosity of higher than about 100 mPa·s at 20° C. is applied as it is, the resulting film is likely to have an excessively large thickness. Accordingly the lubricant for use in coating is used as dissolved in a solvent. When the compound of the present invention is applied as dissolved in a solvent, the film thickness to be obtained is easy to control in the case where the present compound serves singly as a lubricant and also in the case where the compound is used as mixed with other lubricant. The concentration varies with the method and conditions of application, mixing ratio, etc. The lubricant film of the present invention is preferably 5 to 15 Å in thickness.

In order to assure the lubricant of improved adhesion to the ground layer, the lubricant applied can be subjected to heat treatment or ultraviolet treatment. The heat treatment is conducted at 60 to 160° C., preferably at 80 to 160° C. The ultraviolet treatment is conducted using ultraviolet rays of 185 nm and 254 nm in main wavelength.

The magnetic disk of the invention can be applied to a magnetic disk apparatus which can accommodate the disk and which is provided with a magnetic disk drive including a head for recording, reproducing and erasing information and a motor for rotating the disk; and with a control system for controlling the drive.

The magnetic disk of the invention and the magnetic disk apparatus produced using the magnetic disk thereof can be applied for the following: electronic computers, and outer memories for word processors; and can be also applied in navigation systems, games, cellular phone, PHS (personal handyphone system) and like instruments and machines and inner and outer memories for prevention of crimes in buildings, and for management/control systems of power plants.

BRIEF DESCRIPTION OF THE DRAWING

FIG. 1 is a section view showing the structure of the magnetic disk of the invention.

EXAMPLES

The invention will be described in more detail with reference to the following examples to which, however, the invention is not limited.

Example 1

Preparation of $CH_3O\text{—}C_6H_4O\text{—}CH_2CH(OH)$ $CH_2OCH_2\text{—}CF_2CF_2O\text{—}(CF_2CF_2CF_2O)_z$ $CF_2CF_2CH_2\text{—}O\text{—}CH_2CH(OH)CH_2\text{—}OC_6H_4\text{—}$ $O\text{—}CH_3$ (Compound 1)

t-Butanol (45 g), 96 g of a fluoropolyether of the formula 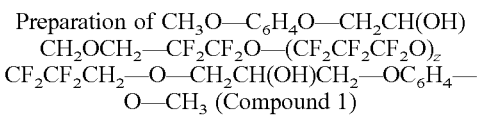

which is 1805 in number average molecular weight and 1.27 in molecular weight distribution, potassium t-butoxide (0.5 g) and glycidyl 4-methoxyphenyl ether (15 g) were stirred at 70° C. in an argon atmosphere for 14 hours. The mixture was thereafter washed with water, dewatered and purified by distillation, affording 90 g of Compound 1.

Compound 1 was a colorless transparent liquid and 1.75 g/cm³ in density at 20° C. Compound 1 was identified by NMR with the result shown.

$^{19}$F-NMR (solvent: none, reference material: OCF$_2$CF$_2$CF$_2$O in the obtained product being taken as -129.7 ppm)
δ=-129.7 ppm
[20F, —OCF$_2$CF$_2$CF$_2$O—]
δ=-83.7
[40F, —OCF$_2$CF$_2$CF$_2$O—]
δ=-124.2 ppm
[4F, —OCF$_2$CF$_2$CH$_2$OCH$_2$CH(OH)CH$_2$— O—C$_6$H$_4$—CH$_3$]
δ=-86.5 ppm
[4F, —OCF$_2$CF$_2$CH$_2$OCH$_2$CH(OH)CH$_2$—O— C$_6$H$_4$—OCH$_3$]
Z=6.3
$^{1}$H-NMR (solvent: none, reference material: D$_2$O)
δ=3.2~3.8 ppm
[22H, H$_3$CO—C$_6$H$_4$O—CH$_2$CH(OH)CH$_2$O—CH$_2$CF$_2$CF$_2$O(CF$_2$CF$_2$CF$_2$O)$_z$CF$_2$CF$_2$CH$_2$—OCH$_2$CH(OH)CH$_2$—OC$_6$H$_4$—OCH$_3$]
δ=6.1 ppm, 6.7 ppm
[8H, —OCF$_2$CF$_2$CH$_2$OCH$_2$CH(OH)CH$_2$—C$_6$H$_4$—OCH$_3$]

Example 2

Preparation of CH$_3$O—C$_6$H$_4$O—CH$_2$CH(OH)CH$_2$OCH$_2$—CF$_2$CF$_2$CF$_2$O(CF$_2$CF$_2$CF$_2$CF$_2$O)$_n$CF$_2$CF$_2$CF$_2$—CH$_2$O—CH$_2$CH(OH)CH$_2$—OC$_6$H$_4$—O—CH$_3$ (Compound 2)

The reaction was conducted in the same manner as in Example 1 except that a fluoropolyether of the formula HO—CH$_2$CF$_2$CF$_2$CF$_2$O(CF$_2$CF$_2$CF$_2$CF$_2$O)$_n$CF$_2$CF$_2$CF$_2$—CH$_2$—OH is used in place of the fluoropolyether of the formula HO—CH$_2$CF$_2$CF$_2$O—(CF$_2$CF$_2$CF$_2$O)$_z$CF$_2$CF$_2$—CH$_2$—OH used in Example 1, affording 61 g of Compound 2.

Compound 2 was a colorless transparent liquid and 1.70 g/cm³ in density at 20° C. Compound 2 was identified by NMR with the result shown.

$^{19}$F-NMR (solvent: none, reference material: OCF$_2$CF$_2$CF$_2$CF$_2$O in the obtained product being taken as -125.8 ppm):
δ=-83.7 ppm
[16F, —OCF$_2$CF$_2$CF$_2$CF$_2$O—, —OCF$_2$CF$_2$CH$_2$OCH$_2$CH(OH)CH$_2$—O—C$_6$H$_4$—OCH$_3$],
δ=-123.3 ppm
[4F, —OCF$_2$CF$_2$CF$_2$CH$_2$OCH$_2$CH(OH)CH$_2$—O—C$_6$H$_4$—OCH$_3$],
δ=-125.8 ppm
[12F, —OCF$_2$CF$_2$CF$_2$CF$_2$O—],
δ=-127.6 ppm
[4F, —OCF$_2$CF$_2$CF$_2$CH$_2$OCH$_2$CH(OH)CH$_2$—C$_6$H$_4$—OCH$_3$]
N=3.0
$^{1}$H-NMR (solvent: none, reference material: D$_2$O)
δ=3.2~3.8 ppm
[22H, CH$_3$O—C$_6$H$_4$O—CH$_2$CH(OH)CH$_2$O—CH$_2$CF$_2$CF$_2$CF$_2$O(CF$_2$CF$_2$CF$_2$O)$_z$CF$_2$CF$_2$CF$_2$CH$_2$—O—OCH$_2$CH(OH)CH$_2$—OC$_6$H$_4$—OCH$_3$]
δ=6.1 ppm, 6.7 ppm
[8H, —OCF$_2$CH$_2$OCH$_2$CH(OH)CH$_2$—C$_6$H$_4$—OCH$_3$]

Example 3

Evaluation of Reat Resistance

A lubricant was checked for heat resistance by measuring a temperature when the lubricant decreased 10 percent in weight by heated in an atmosphere of nitrogen at a rate of 2° C./minute using a thermal analyzer (TG/TDA).

Example 4

Measurement of Bonded Ratio

Lubricant 1 prepared in Example 1 was dissolved in Vertrel-XF, product of DuPont. A magnetic disk, 2.5 inches in diameter, was immersed in the solution for 1 minute and then withdrawn at a rate of 2 mm/s. The disk coated with the lubricant was thereafter held for 10 to 20 seconds in an ultraviolet irradiator equipped with a low-pressure mercury lamp which emits UV light of wavelength of 185 nm and 254 nm. At this irradiation, the air inside of the ultraviolet irradiator was substituted by nitrogen beforehand to prevent the formation of ozone. The average film thickness of the compound on the disk was subsequently measured by a Fourier Transform Infrared Spectrometer (FT-IR). This film thickness was taken as f Å. Next, the disk was immersed in Vertrel-XF for 10 minutes, withdrawn at a rate of 10 mm/s and thereafter allowed to stand at room temperature for the evaporation of the solvent. The compound remaining on the disk was thereafter checked by FT-IR for average film thickness. This film thickness was taken as b Å. The bonded ratio generally in use was used as an indicator for showing the strength of adhesion of the film to the disk. The bonded ratio was expressed by the equation given below.

$$\text{Bonded ratio (\%)}=100\times b/f$$

Example 5

Measurement of Decomposition Resistance to Aluminum Oxide

A sample was used for evaluation which was prepared from each of Compounds 1 and 2, by adding 20 wt. % of Al$_2$O$_3$ to the lubricant, intensely shaking the mixture and thereafter thoroughly agitating the mixture with ultrasonic waves. The sample was checked for decomposition resistance using a thermal analyzer (TG/TDA). The sample was heated at 250° C. for 100 minutes, and the weight reduction (B) of the lubricant was measured. For comparison, 20 mg of each of Compounds 1 and 2 was thermally analyzed in the same manner as above with the exception of adding no Al$_2$O$_3$ to obtain the weight reduction (C). Decomposition Resistance was evaluated by (B-C).

Also used for comparison were Lubricant 3 having hydroxyl at opposite terminals, and Lubricant 4 having aromatic group at opposite terminals of a perfluoropolyether and Fomblin structure.

HO—CH$_2$CH(OH)CH$_2$OCH$_2$—CF$_2$O(CF$_2$CF$_2$O)$_x$(CF$_2$O)$_y$CF$_2$—CH$_2$—CH$_2$CH(OH)CH$_2$OH  (Lubricant 3)

wherein x is 9.8, y is 9.7, and 1.20 in molecular weight distribution.

CH$_3$O—C$_6$H$_4$O—CH$_2$CH(OH)CH$_2$OCH$_2$—CF$_2$O(CF$_2$CF$_2$O)$_v$(CF$_2$O)$_w$CF$_2$—CH$_2$—O—CH$_2$CH(OH)CH$_2$—OC$_6$H$_4$O—CH$_3$ (Lubricant 4)

wherein v is 10.1, w is 10.9, and 1.18 in molecular weight distribution.

Table 1 shows the evaluation of bonded ratio, heat resistance and decomposition resistance to aluminum oxide These results indicate that the perfluoropolyether compounds of the invention having aromatic group at opposite terminals have superior effect in bonded ratio, heat resistance and decomposition resistance than that of the perfluoropolyether compound having hydroxyl at opposite terminals, or that of a compound having aromatic group at opposite terminals of a perfluoropolyether and Fomblin structure.

TABLE 1

| Specimen | Bonded ratio (%) | Heat resistance (° C.) | Decomposition Resistance to aluminum oxide (%) |
|---|---|---|---|
| Compound 1 | 88 | 300 | 3 |
| Compound 2 | 85 | 302 | 3 |
| Lubricant 3 | 80 | 224 | 31 |
| Lubricant 4 | 82 | 252 | <15 |

Example 6

Preparation of Magnetic Disk

Each of Compounds 1 and 2 obtained in examples was dissolved in Vertrel-XF, product of DuPont. The solution was 0.05 wt. % in the concentration of Compounds 1 and 2. A magnetic disk, 2.5 inches in diameter, was immersed in the solution for 1 minute and then withdrawn at a rate of 2 mm/s. The disk was thereafter dried at 150° C. for 10 minutes. The coated compound was thereafter checked by FT-IR for film thickness.

Table 2 shows the results. It was confirmed that the magnetic disk can be obtained which is coated with the present compound, and has higher decomposition resistance and a smaller mono-layer thickness.

TABLE 2

| Specimen | Film thickness (Å) |
|---|---|
| Compound 1 | 11 |
| Compound 2 | 11 |

INDUSTRIAL APPLICABILITY

The fluoropolyether compounds of the invention having an aromatic group are highly stable to heat compared with the conventionally used compounds having —(CF$_2$O)n(CF$_2$CF$_2$O)m-structure (Fomblin structure). Thus, it is possible to provide a lubricating film which is hardly deteriorated with use under high heat environment for a long period of time.

EXPLANATION OF THE SYMBOL

1: substrate;
2: recording layer;
3: protective layer;
4: lubricant layer

The invention claimed is:

1. A compound of the formula (1)

R$^1$—C$_6$H$_4$O—CH$_2$CH(OH)CH$_2$OCH$_2$—R$^2$—CH$_2$—O—CH$_2$CH(OH)CH$_2$—OC$_6$H$_4$—R$^1$    (1)

wherein R$^1$ is alkoxyl having 1 to 4 carbon atoms, amino or amido, R$^2$ is —CF$_2$CF$_2$O(CF$_2$CF$_2$CF$_2$O)$_z$CF$_2$CF$_2$— or —CF$_2$CF$_2$CF$_2$O(CF$_2$CF$_2$CF$_2$CF$_2$O)$_n$CF$_2$CF$_2$CF$_2$—, z is a real number of 1 to 15, n is a real number of 0 to 4.

2. A compound as defined in claim 1 wherein z is a real number of 1 to 10.

3. A compound as defined in claim 1 wherein R$^2$ is —CF$_2$CF$_2$O(CF$_2$CF$_2$CF$_2$O)$_z$CF$_2$CF$_2$—, z is a real number of 1 to 15.

4. A compound as defined in claim 1 wherein R$^2$ is —CF$_2$CF$_2$CF$_2$O(CF$_2$CF$_2$CF$_2$CF$_2$O)$_n$CF$_2$CF$_2$CF$_2$—, n is a real number of 0 to 4.

5. A lubricant containing a compound of the formula (1)

R$^1$—C$_6$H$_4$O—CH$_2$CH(OH)CH$_2$OCH$_2$—R$^2$—CH$_2$—O—CH$_2$CH(OH)CH$_2$—OC$_6$H$_4$—R$^1$    (1)

wherein R$^1$ is alkoxyl having 1 to 4 carbon atoms, amino or amido, R$^2$ is —CF$_2$CF$_2$O(CF$_2$CF$_2$CF$_2$O)$_z$CF$_2$CF$_2$— or —CF$_2$CF$_2$CF$_2$O(CF$_2$CF$_2$CF$_2$CF$_2$O)$_n$CF$_2$CF$_2$CF$_2$—, z is a real number of 1 to 15, n is a real number of 0 to 4.

6. A lubricant as defined in claim 5 wherein z is a real number of 1 to 10.

7. A magnetic disk comprising at least a recording layer and a protective layer formed over a substrate, and a lubricating layer formed over the resulting surface, the lubricating layer containing a compound of the formula (1)

R$^1$—C$_6$H$_4$O—CH$_2$CH(OH)CH$_2$OCH$_2$—R$^2$—CH$_2$—O—CH$_2$CH(OH)CH$_2$—OC$_6$H$_4$—R$^1$    (1)

wherein R$^1$ is alkoxyl having 1 to 4 carbon atoms, amino or amido, R$^2$ is —CF$_2$CF$_2$O(CF$_2$CF$_2$CF$_2$O)$_z$CF$_2$CF$_2$— or —CF$_2$CF$_2$CF$_2$O(CF$_2$CF$_2$CF$_2$CF$_2$O)$_n$CF$_2$CF$_2$CF$_2$—, z is a real number of 1 to 15, n is a real number of 0 to 4.

8. A magnetic disk as defined in claim 7 wherein z is a real number of 1 to 10.

* * * * *